(12) United States Patent
Bauer et al.

(10) Patent No.: US 12,056,907 B2
(45) Date of Patent: Aug. 6, 2024

(54) LIVE CALIBRATION

(71) Applicant: HOYA CORPORATION, Tokyo (JP)

(72) Inventors: Florian Bauer, Friedberg (DE);
Michael Walz, Friedberg (DE)

(73) Assignee: HOYA CORPORATION, Tokyo (JP)

( * ) Notice: Subject to any disclaimer, the term of this patent is extended or adjusted under 35 U.S.C. 154(b) by 135 days.

(21) Appl. No.: 17/785,247

(22) PCT Filed: Dec. 9, 2020

(86) PCT No.: PCT/IB2020/061675
§ 371 (c)(1),
(2) Date: Jun. 14, 2022

(87) PCT Pub. No.: WO2021/124022
PCT Pub. Date: Jun. 24, 2021

(65) Prior Publication Data
US 2023/0029348 A1    Jan. 26, 2023

(30) Foreign Application Priority Data

Dec. 16, 2019  (DE) .................. 10 2019 134 473 .5

(51) Int. Cl.
*G06V 10/141* (2022.01)
*A61B 1/00* (2006.01)
(Continued)

(52) U.S. Cl.
CPC ........ *G06V 10/141* (2022.01); *A61B 1/00009* (2013.01); *A61B 1/00057* (2013.01);
(Continued)

(58) Field of Classification Search
None
See application file for complete search history.

(56) References Cited

U.S. PATENT DOCUMENTS 7,136,100 B1 * 11/2006 Kato .................. H04N 25/63
348/241
7,349,048 B1 * 3/2008 Berman ............. H04N 9/3105
349/5
(Continued)

FOREIGN PATENT DOCUMENTS

| JP | H06-54262 A | 2/1994 |
| JP | 2006-279690 A | 10/2006 |

OTHER PUBLICATIONS

Office Action issued in Japanese Patent Application No. 2022-536946, dated Aug. 8, 2023, together with an English translation.
(Continued)

*Primary Examiner* — Mark T Monk
(74) *Attorney, Agent, or Firm* — GREENBLUM & BERNSTEIN, P.L.C.

(57) ABSTRACT

A device includes an offset subtraction unit; an image sensor which receives, for each of a plurality of bright frames, a respective image signal obtained during a respective exposure time of the image sensor, and transmits the same to the offset subtraction unit, and receives, for a dark frame, a respective image signal obtained during a respective exposure time of the image sensor, and transmits the same to the offset subtraction unit; and a control unit which ensures that the image sensor alternately transmits a number of bright frames and one dark frame to the offset subtraction unit. An amount of light by which the respective image signal for each of the bright frames is generated is larger than an amount of light by which the respective image signal for the dark frame is generated; and the offset subtraction unit obtains an offset and subtracts the offset from a signal.

13 Claims, 5 Drawing Sheets

(51) Int. Cl.
*A61B 1/06* (2006.01)
*G06V 10/60* (2022.01)
*H04N 23/50* (2023.01)
*H04N 23/72* (2023.01)
*H04N 23/74* (2023.01)
*H04N 23/75* (2023.01)
*H04N 23/81* (2023.01)
*H04N 25/63* (2023.01)

(52) U.S. Cl.
CPC ............ *A61B 1/0655* (2022.02); *G06V 10/60* (2022.01); *H04N 23/555* (2023.01); *H04N 23/72* (2023.01); *H04N 23/74* (2023.01); *H04N 23/75* (2023.01); *H04N 25/63* (2023.01); *G06T 2207/10016* (2013.01); *G06T 2207/10068* (2013.01); *G06T 2207/10144* (2013.01); *G06T 2207/10152* (2013.01); *G06T 2207/30004* (2013.01); *H04N 23/81* (2023.01)

(56) References Cited

U.S. PATENT DOCUMENTS

| | | | |
|---|---|---|---|
| 2005/0110895 A1* | 5/2005 | Masuyama | G02B 21/365 |
| | | | 348/E5.079 |
| 2008/0015446 A1 | 1/2008 | Mahmood et al. | |
| 2009/0147078 A1 | 6/2009 | Tani et al. | |
| 2009/0213211 A1 | 8/2009 | Bayer et al. | |
| 2019/0191974 A1* | 6/2019 | Talbert | G01J 3/0208 |

OTHER PUBLICATIONS

International Search Report issued in International Bureau of WIPO Patent Application No. PCT/IB2020/061675, dated Feb. 23, 2021.

* cited by examiner

LIVE CALIBRATION

The invention relates to a method for calibrating image sensor data, especially in connection with endoscopes.

STATE OF THE ART

Optical sensors usually show spatial inhomogeneities in the signal offset (black level, dark level). Said inhomogeneities may vary over time and may also depend on the operating environment. The inhomogeneities may originate from the sensor itself, the electronics thereof, and/or the line transmitting the signal from the sensor to the analog-to-digital converter. In the latter case, the spatial structure is usually independent of the sensor cell, thus resulting in a vertical stripe pattern. In some cases, the inhomogeneities have such intensity that they need to be compensated. Compensating such errors usually involves a calibration step in which the inhomogeneities are detected in a controlled environment and are stored in the sensor device. Then these data are used during recording or during image processing to compensate the spatial structures of the inhomogeneities.

This approach of calibration shows several drawbacks.
(1.) For the production an additional step is necessary which results in increased costs for each sensor device.
(2.) The calibration data have to be stored in the sensor device. Unless such storage unit is provided, a space is required for this purpose, and the costs per unit will increase.
(3.) The calibration in the controlled environment does not consider each possible operating environment or each possible combination with different hardware for the sensor, the line, the processing unit and the respective terminals.
(4.) Repeating the calibration at certain time intervals requires dedicated logistics and infrastructure.

SUMMARY OF THE INVENTION

It is an object of the invention to improve the state of the art.

The invention provides:
A device comprising
an offset subtraction unit;
an image sensor which is configured to receive, for each of a plurality of bright frames, a respective image signal obtained by an optical imaging of at least part of a field of view of an imaging device during a respective exposure time of the image sensor, and to transmit the same to the offset subtraction unit at a first frame rate, and which is configured to receive, for at least one dark frame, a respective image signal obtained by the optical imaging of the at least part of the field of view of the imaging device during a respective exposure time of the image sensor, and to transmit the same to the offset subtraction unit at a second frame rate;
a control unit which is configured to ensure that the image sensor alternately transmits a number of bright frames and at least one dark frame to the offset subtraction unit, wherein
the control unit is configured to ensure that, on the assumption that a scene in the at least part of the field of view of the imaging device is equal in the exposure time for the at least one dark frame and in the respective exposure time of each of the bright frames, a respective amount of light which is detected by the image sensor in the respective exposure time and by which the respective image signal for each of the bright frames is generated, is larger than a respective amount of light which is detected by the image sensor in the respective exposure time and by which the respective image signal for the at least one dark frame is generated;
the offset subtraction unit is configured to obtain an offset based on the image signal of the at least one dark frame, to subtract the offset from a signal based on an image signal of one of the bright frames so as to obtain a calibrated signal, and to provide the calibrated signal for further processing,
wherein the at least one dark frame and the number of bright frames constitute a sequence of frames directly following each other in time.

In this way, at least one of the following advantages will be achieved:
no additional step is required for producing a sensor device;
the calibration corresponds to the respective operating environment and hardware; and
logistics and/or infrastructure for repeating the calibration is not required.

DETAILED DESCRIPTION OF EMBODIMENTS

While in the following detailed description a method is described, the description also refers to devices which are configured to carry out the method. Correspondingly, while in the following detailed description a device which is configured to carry out a method is described, the description also refers to the method itself. In the methods, the use in a surgical or therapeutical application of the human or animal body or diagnosing processes carried out on human or animal bodies can be excluded. Several devices according to the invention may be suited for said applications or processes, however.

For solving the afore-mentioned problems, embodiments of the invention provide a "live calibration". In live calibration, a frame is used, at regular intervals or due to particular events, to record a dark image rather than to record an image of the respective scene ("bright frame"). Said frame ("dark frame") or an average value formed of several of such dark frames is used to calibrate the bright frames.

Here, "scene" is understood to be the object space (viz. especially the objects, the arrangement thereof and the background) which the sensor records. The term also includes the illumination of the object space, unless it is controlled by a device according to several embodiments of the invention.

Accordingly, there are three main variants: the first main variant of the invention is primarily useful, when the image sensor is used in dark environments. One example hereof is an endoscope which is inserted e.g. into a cavity of a human or animal body or into a line. In this environment it is dark so that the endoscope carries along its own light source for illuminating the scene. The light source may be e.g. one or more LED(s) or an exit end of a glass fiber which is connected, at the proximal end of the endoscope, to a light source, at the endoscope tip at the distal end of the endoscope. According to this main variant, during the exposure time of the dark frame the illumination is switched off or is at least reduced as compared to the bright frames. Therefore, the sensor only records a dark image. The latter is used for calibration in several embodiments of the invention.

While the first main variant requires a dark scene (at least the light intensity detected by the sensor during the exposure time of the dark frame should be substantially less than the light intensity detected by the sensor during a bright frame), according to the second and third main variants the environment can as well be relatively bright.

Figure 4:
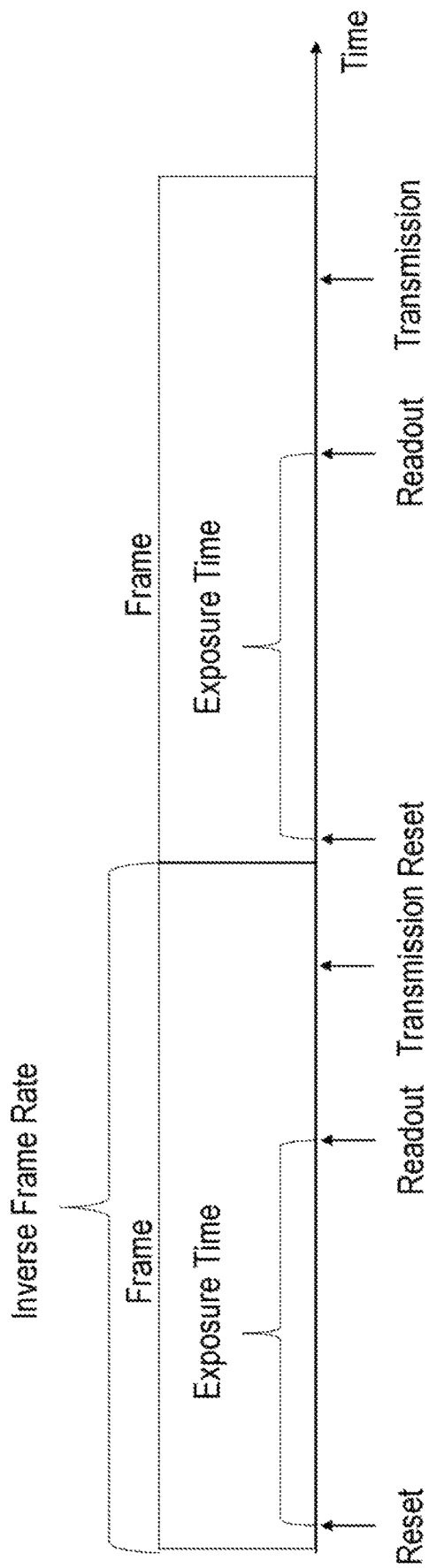
FIG. 4 illustrates the terms of frame and exposure time.

FIG. 4 explains the terms of frame (or, resp., frame rate and inverse frame rate) and of exposure time. FIG. 4 illustrates said terms using the example of a pixel of the sensor. If the image sensor has plural pixels, the times for other pixels may coincide with those of the one pixel or may be shifted vis-à-vis the same.

The sensor transmits its respective image signal once for each frame. The time interval from one transmission to the next is the inverse frame rate. The reciprocal thereof is the frame rate. Herefrom the exposure time for each frame has to be distinguished. The exposure time is the time after a reset of the pixel to the readout of the signal from the pixel. Unless the sensor intermediately stores the read-out signal, it is immediately transmitted for further evaluation (e.g. A/D conversion). In this case, the time of readout coincides with the time of transfer. If an intermediate storage takes place, the transfer takes place after the readout, as illustrated in FIG. 4.

In a bright frame, the exposure time may only be insignificantly shorter than the inverse frame rate, for example. For a frame rate of 30 images per second, for example, it may amount to about 33 msec. However, the exposure time may also be significantly reduced as compared to the inverse frame rate. It may be half of the inverse frame rate (e.g. for motion pictures). In endoscopy, in cases where motion blur should be avoided, it may be even shorter (in the range of ⅕ of the inverse frame rate or in the magnitude of several milliseconds). The minimum exposure time is a characteristic of the respective sensor.

In accordance with the second main variant of the invention, the exposure time of the dark frame is reduced as compared to the exposure time of the bright frames. For example, the exposure time in the dark frame may be shorter by a factor 2, preferred by a factor 5, even more preferred by a factor 10, yet even more preferred by a factor 50, and yet more preferred by a factor 500, than the exposure time in a normal frame. The maximum factor may be 10000, preferred 5000, and even more preferred 1000, because otherwise the amount of light detected by the sensor becomes too small. The exposure time of the dark frame may even be 0. For this reason, the amount of light detected by the sensor during the exposure time of the dark frame, on the assumption that the scene (including illumination thereof) is unchanged, is definitely smaller than the amount of light detected by the sensor during the exposure time of a bright frame. Consequently, several embodiments of the invention make use of such dark frame for calibrating the inhomogeneities of the sensor and/or the electronics thereof and/or the line.

In accordance with a third main variant of the invention, the amount of light detected by the sensor for each time unit while the scene is unchanged (including unchanged illumination of the scene) is controlled by a variable diaphragm. Such diaphragm may be, e.g., a mechanical diaphragm. Due to the short inverse frame rates, however, in numerous cases probably a mechanical diaphragm is too slow. Alternatively, e.g. a stroboscope diaphragm that rotates at an appropriate speed or an electronic diaphragm can be used. An electronic diaphragm may be constructed, e.g., of juxtaposed semiconductor light valves as they are employed in LCD screens.

During a dark frame, the diaphragm aperture is smaller than during a bright frame. The diaphragm is preferred to be closed during a dark frame. That is to say, a camera shutter in this case is considered to be a special case of a diaphragm.

The first to third main variants may be combined with each other at will to improve the relative darkness in a dark frame.

According to embodiments of the invention, the device records at least one dark frame and then plural bright frames. However, also plural dark frames or alternately one dark frame and one bright frame can be recorded. Typically, the dark frame or dark frames is/are periodically recorded. In addition, or alternatively, the dark frame or dark frames can also be recorded because of a predetermined event. For example, the dark frame or dark frames can be recorded because of an operator's input or when the scene (especially the (external) illumination thereof) is found to have changed by more than one fixed threshold, or when the multiplier of a signal amplifier and, thus, the intensity of the offset has changed.

Figure 3:
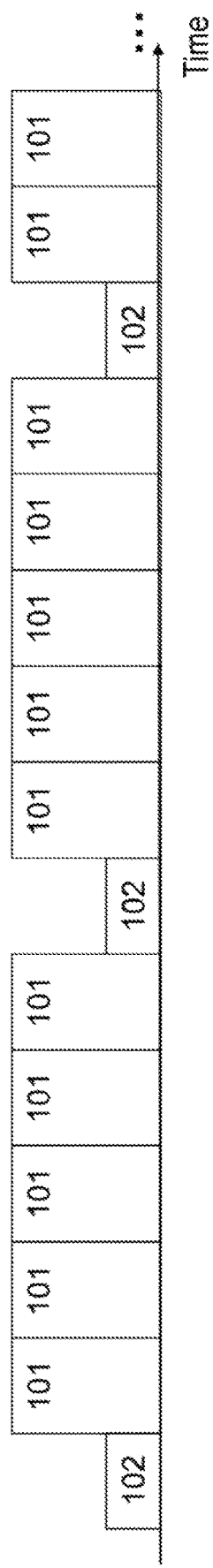
FIG. 3 shows a record sequence of bright and dark frames according to an embodiment of the invention.

FIG. 3 illustrates an example of a sequence of frames (bright frames 101 and dark frames 102) according to an embodiment of the invention. In this example, a dark frame 102 and then a certain number of bright frames 101 (here: 5 bright frames) are generated directly following each other. This sequence is periodically repeated, possibly interrupted by dark frame records because of a predefined event. The offset for subsequent bright frames 101 is at least based on the signal of the preceding dark frame 102.

The dark frame is not shown during image processing and, resp., display but is merely used for calibration. In one example, the intensity of a dark frame is subtracted from the intensity of the subsequent normal frame.

If the image sensor includes plural pixels, calibration can by carried out pixel by pixel or pixel group by pixel group. Pixel by pixel means that for each pixel a separate offset is calculated and subtracted from the pixel value of the respective pixel of a bright frame. Pixel group by pixel group means that the pixels are divided into groups, and the same offset is subtracted from the respective pixel value of each pixel of one group of a bright frame. Said offset may be obtained by averaging over all pixels within the group of a dark frame. The groups may be arranged in any order on the sensor surface. For example, the pixels of one column may form one group, or the pixels are divided, in a chessboard pattern, into groups of n*m neighboring pixels each (e.g. 2*2 pixels, or 2*3 pixels, or 3*2 pixels, etc.). In an extreme example, one group may also contain all pixels of the image sensor.

In another example, plural dark frames are recorded. Said dark frames then are processed together, e.g. by simple averaging or weighted averaging, wherein typically the latest dark frames are weighted more heavily than the earlier dark frames. This may help reduce noise in the calibration data. Further, by comparing the various dark frames, it can be detected when disturbing signals such as e.g. a changed illumination by an external light source are present, and, in this case, the respective dark frame will not be used at all or will be used with little weight only. The moving averaging allows the calibration to be adapted also automatically to the respective operating environment.

In some embodiments, especially if the compensation of a stripe pattern in an image sensor including plural pixels arranged in lines and columns is concerned, an averaging is performed over several neighboring pixels of each column (or each line) of the same frame. This averaging can be combined with the averaging over plural frames.

One example to which an embodiment of the invention is applied is an endoscope. However, the invention is not limited to endoscopes for insertion into a human body. It may also be used, for example, for endoscopes that are inserted into pipelines. Nor is the invention limited to endoscopes, it may rather be used basically for all types of image sensors.

Figure 1:
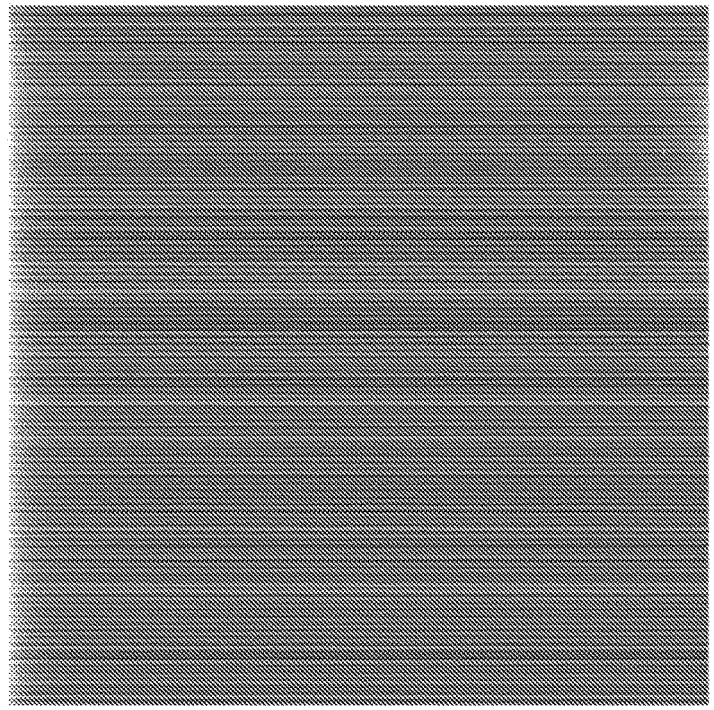
FIG. 1 on the left shows an image record of a scene and on the right shows the image record of a dark image (intensified by the factor 10 and averaged over plural frames) according to the state of the art.
Figure 1:
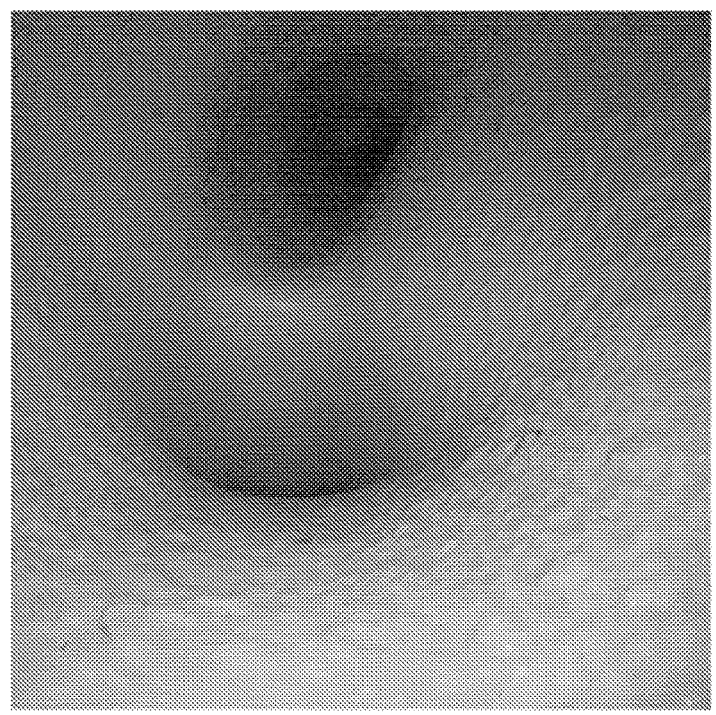

For example, in many endoscopes the A/D converter (analog-to-digital converter) can be disposed on the same chip as the image sensor in the endoscope tip at the distal end of the endoscope, whereas in other endoscopes it is provided at the proximal end of the endoscope. In particular in the latter case, due to the large distance of the image sensor from the A/D converter and the control unit, the signal interference is significant. A main source of interference (both in endoscopes comprising the A/D converter at the distal end and in endoscopes comprising the A/D converter at the proximal end) is the clock whose signals interfere with the image signal (resistive and/or capacitive coupling) which entails a column-dependent offset that results, in the image, in a vertical stripe pattern (see FIG. 1). FIG. 1 on the left shows an image record of a scene (bright frame) and on the right shows the image record of a dark image (intensified by the factor 10 and averaged over plural dark frames). The stripe pattern is clearly evident both in the record of the scene and in the dark image.

Figure 2:
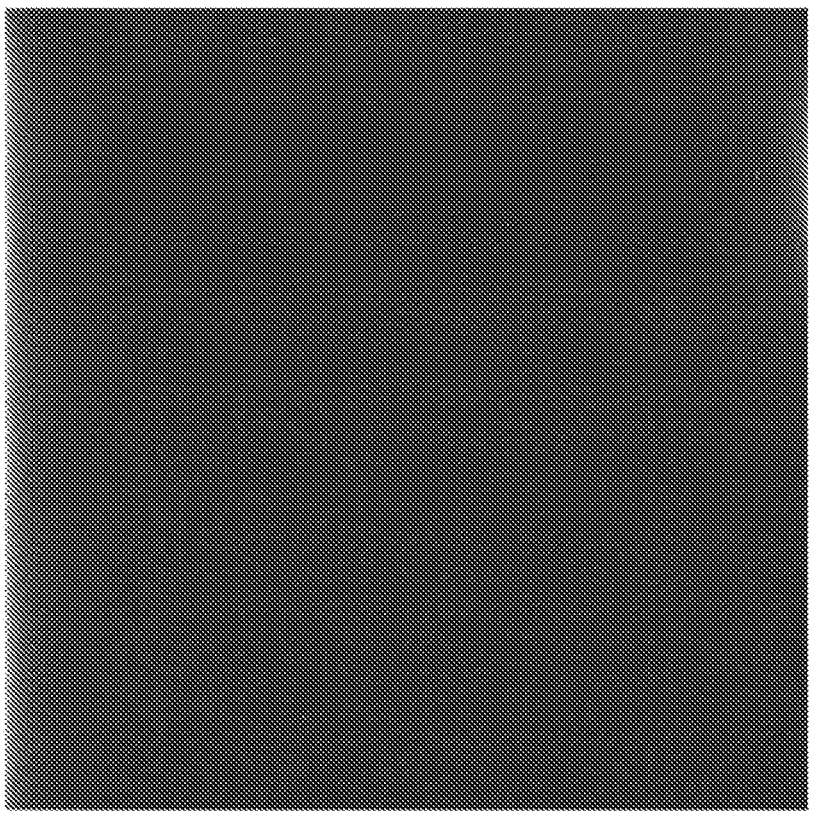
FIG. 2 on the left shows an image record of a scene and on the right the image record of a dark image (intensified by the factor 10 and averaged over plural frames), after offset compensation according to an embodiment of the invention.
Figure 2:

Therefore, according to embodiments of the invention, dark frames are regularly recorded, as explained in the foregoing. This allows the signal offset to be estimated and then to be compensated during image processing, resulting in an image in which only a minimum stripe pattern is visible (see FIG. 2). FIG. 2 corresponds to FIG. 1, with the exception that both in the image of the scene on the left and in the dark image on the right the offset was compensated by moving averaging over plural dark frames. The stripe pattern of FIG. 1 is practically no longer visible in FIG. 2, and, thus, the quality of the record of the scene is significantly improved.

The dark frame in this example can be recorded by switching off the light source of the endoscope for the exposure time of the dark frame. It can also be recorded by setting the exposure time of the dark frame to be substantially shorter than the exposure time of the normal frames. In this example, the exposure time is set to the minimum value of less than 100 µs, whereas the exposure time of a bright frame is several milliseconds. Of preference, during a dark frame both the exposure time of the sensor is minimized and the light source is switched off.

When the sensor (the distal end of the endoscope) is located inside a human or animal body or e.g. inside a pipeline, there is no external light source so that it can be assumed that in the dark frame a dark image is recorded. When the endoscope is located at a place where there might be external light sources, the signal may still be considered to be dark, because the exposure time of the dark frame is substantially shorter than that of a bright frame, and/or, if a variable diaphragm is present, the diaphragm aperture is substantially smaller during the exposure time of the dark frame than is the diaphragm aperture during the exposure time of the bright frame.

As afore-described, for calibration a moving average algorithm over plural dark frames and/or several pixels within a pixel group can be used to obtain calibration data calib. In the following, an example of such algorithm which operates with integers shall be described:

If the pixel value of the dark frame is smaller than a threshold, its value is added to the existing calibration data by means of a moving average. The pixel values pixel are multiplied with 2^globalShift to achieve higher accuracy. In the programming language C, the algorithm for averaging is as follows:

```
if (pixel < threshold)
{
calib *= (1 << avgShift) – 1;
calib += (pixel << globalShift) + (1 < < (avgShift-1));
calib >>= avgShift;
}
```

Preferably, the value of the threshold "threshold" should be selected as Blacklevel+MaxFP, wherein Blacklevel is the black level of the A/D converter and MaxFP is the maximum value which the stripe pattern can assume.

Ignoring pixel values that are higher than the threshold ensures that the calibration data do not exceed said value so that the maximum error in the compensated frame is less than 2*MaxFP.

In this example, the calibration data are calculated pixel by pixel. However, it is also possible for the pixel data to be initially smoothed inside each dark frame.

The calibration data are added to the image data that are transferred via USB e.g. in a predetermined line (e.g. the first line). Prior to the actual image processing, the calibration data are subtracted from the image data, and the first line containing the calibration data is removed.

The invention is not limited to a vertical stripe pattern formed by the readout principle of a typical CCD or CMOS sensor. It can be applied to any offset patterns. The offset patterns are preferred to vary only relatively slowly over time so that they are constant (or substantially constant) over plural dark frames. For example, they should not deviate more than 10% over ten dark frames. A deviation of less than 5% or even less than 2% is more preferred.

Typically, the frame rate is constant for all bright and dark frames during a certain time period and is equal for all of said bright and dark frames. It is not necessary for embodiments of the invention, however, that the frame rate is constant, or that it is equal for bright and dark frames. E.g. some bright frames or dark frames can be transmitted at a higher frame rate and other bright frames or dark frames can be transmitted at a lower frame rate. For example, all bright frames can be transmitted at a (preferably smaller) frame rate different from that of all dark frames during the time period. Of preference, the inverse frame rate (i.e. the time interval between two image signal transmissions from the sensor) for bright frames should be high as compared to the minimum exposure time of the sensor, however, unless it can be ensured that the sensor really is in a dark environment when recording a dark frame.

Depending on the embodiment, the calibration (i.e. subtracting an offset from the image data) can be performed before, during or after the A/D conversion of the sensor signal of a bright frame. When the calibration is performed after the A/D conversion of the sensor signal of the bright frame, the calibration value can be established, where appropriate, from plural dark frames both before and after the A/D conversion of the corresponding sensor signals of the plural dark frames.

In accordance with embodiments of the invention, on the assumption that the scene recorded by the image sensor (including an optional external illumination) is unchanged, a respective amount of light which is detected by the image sensor and by which the respective image signal is generated for each of the bright frames is larger than a respective amount of light which is detected by the image sensor and by which the respective image signal is generated for the at least one dark frame. Of preference, the amount of light for a bright frame is to be twice as large, even more preferred 5 times as large, even more preferred 10 times as large and yet more preferred 100 times as large as for a dark frame. The amount of light detected in a dark frame may also be 0.

Figure 5:
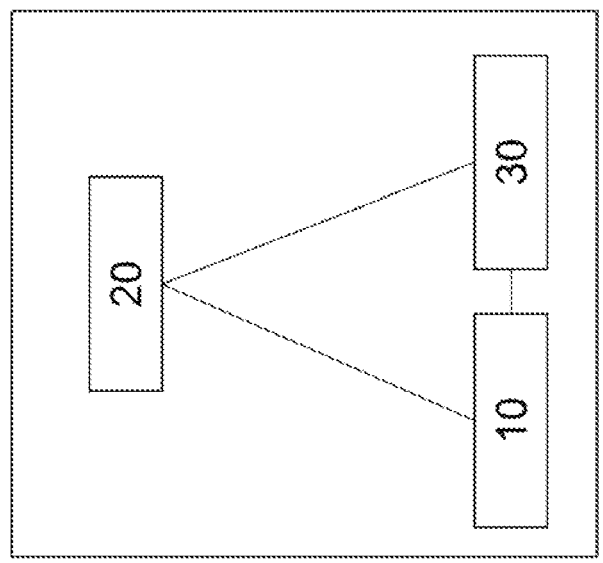
FIG. 5 shows a device according to an embodiment of the invention.

FIG. 5 illustrates a device according to an embodiment of the invention. The device includes an offset subtraction unit 10, an image sensor 20 and a control unit 30.

For each of a plurality of bright frames, the image sensor 20 receives a respective image signal obtained by optical imaging of a scene during a respective exposure time of the image sensor, and transmits the same at a first frame rate to the offset subtraction unit 10. Furthermore, the image sensor 20 receives, for at least one dark frame, a respective image signal obtained by the optical imaging of the scene during a respective exposure time of the image sensor, and transmits the same to the offset subtraction unit 10 at a second frame rate.

The image sensor may be a CCD sensor or a CMOS sensor, for example. The number of the pixels of the sensor is not limited.

The control unit 30 ensures the image sensor to alternately transmit a first number of bright frames and at least one dark frame to the offset subtraction unit 10. Further, the control unit ensures that, on the assumption that the scene (including its (external) illumination) is unchanged, a respective amount of light which is detected by the image sensor 20 in the respective exposure time and by which the respective image signal for each of the bright frames is generated is larger than a respective amount of light which is detected by the image sensor 20 in the respective exposure time and by which the respective image signal for the at least one dark frame is generated. This can be achieved by the control unit e.g. by controlling an internal light source that illuminates the scene, the respective exposure times and/or the size of the aperture of a variable diaphragm.

The offset subtraction unit 10 receives an offset based on the image signal of the at least one dark frame, subtracts the offset from a signal that is based on an image signal of one of the bright frames to obtain a calibrated signal, and provides the calibrated signal for further processing. The signal may be the image signal of a bright frame from the image sensor 10, or a signal which results, e.g. by A/D conversion and/or further processing steps, from the image signal of the bright frame from the image sensor 10. The offset may equally be the corresponding image signal of a dark frame from the image sensor 10, or a signal which results, e.g. by A/D conversion and/or further processing steps (e.g. averaging over plural dark frames), from the corresponding image signal of a dark frame from the image sensor 10.

Figure 6:
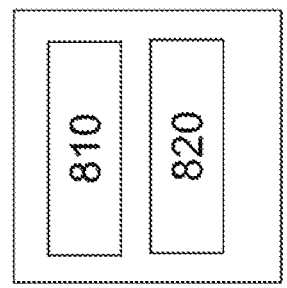
FIG. 6 shows a device that can be used in an embodiment of the invention.

The control unit and the offset subtraction unit as well as a possibly present image processing unit can be in the form of hardware and/or software. They may be implemented in one or more hardware units and/or software units. They may equally be implemented in the cloud. Each of them may also be implemented in one or more computers (e.g. laptop). As illustrated in FIG. 6, they may even be implemented by a processor 810 comprising a memory 820, the memory 820 storing program instructions which ensure that the processor 810 carries out a method according to the invention, when the same are carried out by the processor 810.

It is assumed that generally the amount of light detected by the image sensor is the larger, the larger the amount of light which is incident on the image sensor. For example, the amount of light detected can be proportional to the incident amount of light, or can show gradual saturation with an increasing amount of light.

The invention claimed is:

1. A device comprising:
an offset subtractor;
an image sensor which is configured to receive, for each of a plurality of bright frames, a respective image signal obtained by optical imaging of at least part of a field of view of an imaging device during a respective exposure time of the image sensor, and to transmit the same to the offset subtractor at a first frame rate, and which is configured to receive, for at least one dark frame, a respective image signal obtained by the optical imaging of the at least part of the field of view of the imaging device during a respective exposure time of the image sensor, and to transmit the same to the offset subtractor at a second frame rate;
a light configured to illuminate a scene; and
a controller which is configured to ensure that the image sensor alternately transmits a number of bright frames and at least one dark frame to the offset subtractor, wherein
the controller is configured to ensure that, on the assumption that the scene, which is in the at least part of the field of view of the imaging device is equal in the exposure time for the at least one dark frame and in the respective exposure time of each of the bright frames, a respective amount of light which is detected by the image sensor in the respective exposure time and by which the respective image signal for each of the bright frames is generated, is larger than a respective amount of light which is detected by the image sensor in the respective exposure time and by which the respective image signal for the at least one dark frame is generated,
the offset subtractor is configured to obtain an offset based on the image signal of the at least one dark frame, to subtract the offset from a signal based on an image signal of one of the bright frames so as to obtain a calibrated signal, and to provide the calibrated signal for further processing,
the at least one dark frame and the number of bright frames constitute a sequence of frames directly following each other in time, and
the controller is configured to control the light such that the light illuminates the scene during the respective exposure times of the bright frames at a first light intensity and that the light illuminates the scene during the exposure time of the at least one dark frame at a second light intensity, the second intensity being less than the first intensity.

2. The device according to claim 1, wherein
the control unit is configured to ensure that the sequence of frames directly following each other in time is repeated periodically, each of the sequences directly following a corresponding previous sequence of the sequences in time, and
the offset subtraction unit is configured to obtain, for each of the sequences, a respective offset based on the image signal of the at least one dark frame of the respective sequence, to subtract the offset from a signal based on an image signal of one of the bright frames of the respective sequence so as to obtain a calibrated signal, and to provide the calibrated signal for further processing.

3. The device according to claim 1, wherein
the control unit is configured to ensure that at least one dark frame occurs when there is a predetermined event, and
the offset subtraction unit is configured to obtain, for at least one bright frame following the dark frame, an offset based on the image signal of the at least one dark frame that has occurred due to the predetermined event, to subtract the offset from the signal based on the image signal of the at least one bright frame so as to obtain a calibrated signal, and to provide the calibrated signal for further processing.

4. The device according to claim 1, wherein the offset subtraction unit is configured to obtain the offset by an averaging over the image signals of a plurality of dark frames.

5. The device according to claim 1, wherein
the image sensor has a plurality of pixels, and
the offset subtraction unit is configured to obtain, for each of the pixels, a respective offset based on the image signal of the respective pixel of the at least one dark frame.

6. The device according to claim 5, wherein
the pixels are divided into groups of one or several pixels, and
the offset subtraction unit is configured to obtain a respective offset for each of the groups, and to subtract the respective offset for each of the pixels of the group from a signal of the respective pixel that is based on an image signal of one of the bright frames so as to obtain a calibrated signal of the respective pixel.

7. The device according to claim 6, wherein
the offset subtraction unit is configured to obtain the respective offset for each group by an averaging over the image signals of the pixels of the respective group of the at least one dark frame.

8. An endoscope comprising a device according to claim 1,
wherein the image sensor is located in a tip of the endoscope at the distal end of the endoscope, and the offset subtraction unit is connected to the proximal end of the endoscope.

9. A device comprising:
an offset subtractor;
an image sensor which is configured to receive, for each of a plurality of bright frames, a respective image signal obtained by optical imaging of at least part of a field of view of an imaging device during a respective exposure time of the image sensor, and to transmit the same to the offset subtractor at a first frame rate, and which is configured to receive, for at least one dark frame, a respective image signal obtained by the optical imaging of the at least part of the field of view of the imaging device during a respective exposure time of the image sensor, and to transmit the same to the offset subtractor at a second frame rate;
a light configured to illuminate a scene;
a controller which is configured to ensure that the image sensor alternately transmits a number of bright frames and at least one dark frame to the offset subtractor, wherein
the controller is configured to ensure that, on the assumption that a scene in the at least part of the field of view of the imaging device is equal in the exposure time for the at least one dark frame and in the respective exposure time of each of the bright frames, a respective amount of light which is detected by the image sensor in the respective exposure time and by which the respective image signal for each of the bright frames is generated, is larger than a respective amount of light which is detected by the image sensor in the respective exposure time and by which the respective image signal for the at least one dark frame is generated;
the offset subtractor is configured to obtain an offset based on the image signal of the at least one dark frame, to subtract the offset from a signal based on an image signal of one of the bright frames so as to obtain a calibrated signal, and to provide the calibrated signal for further processing;
the at least one dark frame and the number of bright frames constitute a sequence of frames directly following each other in time; and
the controller is configured to set expose the image sensor to the light emitted from the light while setting the exposure time for the at least one dark frame such that it is shorter than that for each of the bright frames.

10. A device comprising:
an offset subtractor;
an image sensor which is configured to receive, for each of a plurality of bright frames, a respective image signal obtained by optical imaging of at least part of a field of view of an imaging device during a respective exposure time of the image sensor, and to transmit the same to the offset subtractor at a first frame rate, and which is configured to receive, for at least one dark frame, a respective image signal obtained by the optical imaging of the at least part of the field of view of the imaging device during a respective exposure time of the image sensor, and to transmit the same to the offset subtractor at a second frame rate;
a controller which is configured to ensure that the image sensor alternately transmits a number of bright frames and at least one dark frame to the offset subtractor; and
a variable stroboscope diaphragm by which an amount of light incident on the image sensor per time unit is set, wherein
the controller is configured to ensure that, on the assumption that a scene in the at least part of the field of view of the imaging device is equal in the exposure time for the at least one dark frame and in the respective exposure time of each of the bright frames, a respective amount of light which is detected by the image sensor in the respective exposure time and by which the respective image signal for each of the bright frames is generated, is larger than a respective amount of light which is detected by the image sensor in the respective exposure time and by which the respective image signal for the at least one dark frame is generated;

the offset subtractor is configured to obtain an offset based on the image signal of the at least one dark frame, to subtract the offset from a signal based on an image signal of one of the bright frames so as to obtain a calibrated signal, and to provide the calibrated signal for further processing;

the at least one dark frame and the number of bright frames constitute a sequence of frames directly following each other in time; and the controller is configured to control the variable stroboscope diaphragm for each of the bright frames such that it is in a respective first opening state, and is configured to control the variable stroboscope diaphragm for the at least one dark frame such that it is in a respective second opening state, the variable stroboscope diaphragm having a larger aperture in each of the first opening states than in the at least one second opening state.

11. The device according to claim 10, wherein the variable diaphragm is closed in the at least one second opening state.

12. The device according to claim 10, wherein the variable diaphragm is opened in the at least one second opening state so that the respective image signal for the at least one dark frame is obtained by the optical imaging of the scene.

13. The device according to claim 10, wherein the variable stroboscope diaphragm is rotatable.

* * * * *